United States Patent [19]

Clémence et al.

[11] 4,159,986

[45] Jul. 3, 1979

[54] NOVEL THIOPHENE-ACETIC ACIDS

[75] Inventors: François Clémence, Rosny-sous-Bois; Odile Le Martret, Paris, both of France

[73] Assignee: Roussel Uclaf, Paris, France

[21] Appl. No.: 610,110

[22] Filed: Sep. 4, 1975

Related U.S. Application Data

[63] Continuation-in-part of Ser. No. 229,554, Feb. 25, 1972, abandoned, which is a continuation-in-part of Ser. No. 88,125, Nov. 9, 1970, abandoned.

[30] Foreign Application Priority Data

Nov. 12, 1969 [FR] France .................... 69.38734
Mar. 11, 1971 [FR] France .................... 71.08476

[51] Int. Cl.² .................... C07D 333/24; A01N 9/00
[52] U.S. Cl. .................... 260/332.2 A; 424/275
[58] Field of Search ......... 260/332.2 A, 517, 294.8 D; 424/317

[56] References Cited

U.S. PATENT DOCUMENTS

| | | | |
|---|---|---|---|
| 3,466,372 | 9/1969 | Shen | 424/248 |
| 3,560,525 | 2/1971 | Kaltenbronn | 260/332.2 A |
| 3,577,549 | 5/1971 | Jack | 424/317 |
| 3,644,399 | 2/1972 | Brown | 260/326.3 |
| 3,682,964 | 8/1972 | Rousseau | 260/327 |

FOREIGN PATENT DOCUMENTS

| | | | |
|---|---|---|---|
| 1516775 | 2/1968 | France | 260/517 |
| 684682 | 1/1969 | South Africa | 260/517 |

*Primary Examiner*—A. Siegel
*Attorney, Agent, or Firm*—Hammond & Littell

[57] ABSTRACT

Novel thiophene-acetic acid derivatives of the formulae

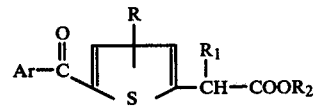

I and

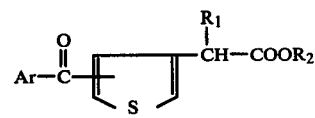

II wherein R is selected from the group consisting of hydrogen and alkyl of 1 to 4 carbon atoms, $R_1$ is selected from the group consisting of lower alkyl of 1 to 4 carbon atoms and hydrogen and $R_2$ is selected from the group consisting of hydrogen, lower alkyl of 1 to 7 carbon atoms and optionally substituted with at least one hydroxy group or an oxygen atoms-containing heterocycle, di-lower alkylamino-lower alkyl, N-heterocyclic alkyl, alkali metals, alkaline earth metals, aluminum and —H,NH (lower alkyl)$_2$ and Ar is selected from the group consisting of phenyl, optionally substituted with at least one member of the group consisting of halogen, trihalogenomethyl, lower alkyl, lower alkoxy and carboxyl, cyclohexyl, thienyl, furyl, tetrahydrofuryl and pyridyl, and in formula II, ArCO is attached to one of the positions α to the sulfur atom, which compounds have analgesic and anti-inflammatory activity and their preparations.

19 Claims, No Drawings

NOVEL THIOPHENE-ACETIC ACIDS

REFERENCE TO PRIOR APPLICATIONS

This application is a continuation-in-part of our copending U.S. Patent Application Ser. No. 229,554, filed Feb. 25, 1972, now abandoned which in turn is a continuation-in-part of U.S. Patent Application Ser. No. 88,125, filed Nov. 9, 1970, now abandoned.

OBJECTS OF THE INVENTION

It is an object of the invention to provide the novel thiophene acetic acid derivatives of formulae I and II.

It is another object of the invention to provide a novel process for the preparation of the thiophene acetic acid derivatives of formulae I and II.

It is an additional object of the invention to provide novel analgesic and anti-inflammatory compositions.

These and other objects and advantages of the invention will become obvious from the following detailed description.

THE INVENTION

The novel thiophene-acetic acid derivatives of the invention have the formulae

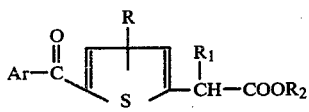   I and

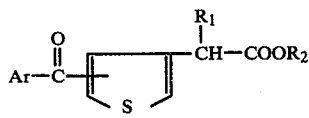   II wherein R is selected from the group consisting of hydrogen and alkyl of 1 to 4 carbon atoms, $R_1$ is selected from the group consisting of lower alkyl of 1 to 4 atoms and hydrogen and $R_2$ is selected from the group consisting of hydrogen, lower alkyl of 1 to 7 carbon atoms and optionally substituted with at least one hydroxy group or an oxygen atoms-containing heterocycle, di-lower alkylamino-lower alkyl, N-heterocyclic alkyl, alkali metals, alkaline earth metals, aluminum and —H,NH(-lower alkyl)$_2$ and Ar is selected from the group consisting of phenyl, optionally substituted with at least one member of the group consisting of halogen, trihalogenomethyl, lower alkyl, lower alkoxy and carboxyl cyclohexyl, thienyl, furyl, tetrahydrofuryl and pyridyl, and in formula II, Ar CO is attached to one of the positions α to the sulfur atom, i.e. in the 2 or 5 position of the thiophene nucleus. Those compounds of formulae I and II, which have at least one asymetrical carbon, may be in the form of racemates or an optically active isomer.

Examples of thiophene-acetic acid derivatives of formula I are 5-benzoyl-thiophene-2-α-methyl acetic acid; 5-(p-chloro-benzoyl)-thiophene-2-α-methyl acetic acid; 5-hexahydrobenzoyl-thiophene-2-α-methyl acetic acid; 5-(α-thenoyl)-thiophene-2-α-methyl acetic acid; 5-benzoyl-thiophene-2-acetic-acid; 5-(m-trifluoromethylbenzoyl)-thiophene-2-acetic acid; 5-(β-nicotinoyl)-thiophebe-2-α-methyl-acetic acid; methyl 5-(m-trifluoromethylbenzoyl)-thiophene-2-acetate; 2,3-dihydroxypropyl 5-(m-trifluoromethylbenzoyl)-thiophene-2-acetate; diethylaminoethyl 5-(p-chlorobenzoyl)-thiophene-2-α-methyl acetate; 5-(α-furoyl)-thiophene-2-α-methyl acetic acid; 2,2-dimethyl-1,3-dioxolane-4-methyl 5-(m-trifluoro-methylbenzoyl)-thiophene-2-acetate; di-isopropylamine salt of 5-benzoyl-thiophene-2-α-methyl acetate acid; methyl 5-benzoyl-thiophene-2-α-methyl acetate; 2,2-dimethyl-1,3-dioxolane-4-methyl 5-benzoyl-thiophene-2-α-methyl acetate; 2,3-dihydroxypropyl 5-benzoyl-thiophene-2-α-methyl acetate; 5-(2′,4′-dichlorobenzoyl)-thiophene-2-α-methyl acetic acid; 3-methyl-5-benzoyl-thiophene-2-α-methyl acetic acid and 4-methyl 5-benzoyl-thiophene-2-acetic acid.

Examples of thiophene-acetic acid derivatives of formula II are 5-benzoyl-thiophene-3-acetic acid; 2-benzoyl-thiophene-3-acetic acid.

The novel process of the invention for the preparation of the thiophene-acetic acid derivatives of formulae I and II comprises reacting, in the presence of a Lewis acid, an acylating derivative of an acid of the formula Ar—COOH wherein Ar has the above definition with a thiophene of the formulae

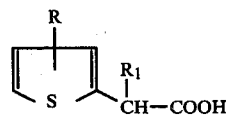   III or

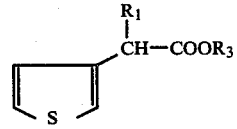   IV wherein R and $R_1$ have the above definitions and $R_3$ represents hydrogen or lower alkyl, to obtain the corresponding compounds of formula I in which $R_2$ is hydrogen or of formula II in which $R_2$ is hydrogen or lower alkyl. The compounds of formula II where $R_2$ is lower alkyl can be saponified to give compounds where $R_2$ is hydrogen. The said compounds of formulae I and II where $R_2$ is hydrogen can be esterified or salified or, when there is at least one asymetrical carbon in the compound, resolved by known processes.

In the preferred embodiment, the Lewis acid is aluminum chloride although other Lewis acids such as stannic chloride, zinc chloride, boron trifluoride, hydrofluoric acid, sulfuric acid, phosphoric acid and phosphorus oxychloride may be used. The reaction is preferably effected in an inert anhydrous organic solvent such as petroleum ether, nitrobenzene, methylene chloride or chloroform. The acylating derivative of the Ar—COOH compound is preferably the acid chloride although other acid halides or the acid anhydride, or a lower alkyl ester, may be used.

When a thiophene-3-acetic acid derivative of formula IV is used as the starting compound in the process of the invention, the acylation reaction leads to a mixture of compounds substituted in the 2 position and in the 5 position (α to the sulfur atom in the thiophene nucleus). The separation of these two isomeric compounds is easily effected by fractional crystallization. Where $R_2$ is lower alkyl, the saponification to obtain the free acid ($R_2$=H) is effected by heating in the presence of an alkaline base.

The esterification of the thiophene acetic acids of formulae I and II (where $R_2$=H) may be effected by reaction of the acid or its esterifying derivatives, such as the acid chloride or acid anhydride, with an alcohol such as lower alkanols, i.e. methanol, ethanol, propanol, tert.-butanol, or aminoalkyl alcohols, such as di-lower alkylamino-lower alkanols, i.e. diethylamino-ethanol or diethylamino-propanol or by transesterification of the lower alkyl esters such as the methyl esters. In this manner, the 2,3-dihydroxypropyl esters may be prepared by transesterification with glycerol actonide in the presence of an alkaline agent such as sodium or sodium amide followed by hydrolysis of the acetonide intermediate with or without isolation thereof to form the 2,3-dihydroxypropyl ester.

The salification may be effected by treating the thiophene acetic acids of formulae I and II with a nontoxic, pharmaceutically acceptable base to form the corresponding salt such as sodium, potassium, aluminum, magnesium, calcium, or diisopropylamine. The resolution of the thiophene-acetic acid derivatives of formulae I and II which have at least one asymetrical carbon may be effected by known means such as with an optically active base to give the optically active compounds.

The novel analgesic and anti-inflammatory compositions of the invention are comprised of at least one compound of formulae I or II and a major amount of a pharmaceutical carrier. These compositions may be in the form of injectable solutions or suspensions in ampoules or multiple dose flacons, in the form of tablets, coated tablets, capsules, syrups, suppositories or ointments.

The compositions are useful for the treatment of muscular, articular or nervous pains, rheumatic ailments, dental pains, zona, migraines, traumatisms, pains from setting of fractures, treatment following painful operations, decubitus aches, and as complementary treatment of fevers or infections or lumbago.

The novel method of combatting pain and inflammations in warm-blooded animals comprises administering to warm-blooded animals a safe and effective amount of at least one compound of formulae I or II. The compounds may be administered orally, transcutaneously, rectally or topically to the skin or mucous membranes. The usual effective daily dose is 0.8 to 8 mg/kg in the adult depending upon the method of administration and the therapeutic indications. The useful dose varies between 0.05 gm and 0.75 gm per day in the adult.

The thiophene-2-acetic acid and the thiophene-3-acetic acid starting materials are described in the literature, the α-alkyl thiophene-acetic acids are obtained by alkylation of the thiophene-acetic acids in the presence of lithium diethylamide.

In the following examples there are described several preferred embodiments to illustrate the invention. However, it should be understood that the invention is not intended to be limited to the specific embodiments.

EXAMPLE 1

5-benzoyl-thiophene-2-α-methyl-acetic acid

A mixture of 10.3 gm of thiophene-2-α-methyl acetic acid [prepared by process of Bercot-Vatteroni,et al, Bull. Soc. Chim. (1961) p. 1820–1], 11.10 gm of benzoyl chloride and a suspension of 23.73 gm of aluminum chloride in 110 cc of chloroform was allowed to stand for 15 minutes and was then poured into a mixture of ice and hydrochloric acid. The chloroform phase was extracted with a 10% aqueous potassium carbonate solution and the aqueous alkaline phase was acidified with N hydrochloric acid and was then extracted with ether. The ether was evaporated off and the residue was crystallized from carbon tetrachloride to obtain a 54% yield of 5-benzoyl-thiophene-2-α-methyl acetic acid melting at 83–85° C. The product occurred in the form of colorless crystals soluble in dilute alkaline solutions, alcohol and ether and insoluble in water.

Analysis: $C_{14}H_{12}O_3S$; molecular weight = 260.30. Calculated: %C 64.59; %H 4.64; %S 12.31. Found: %C 64.30; %H 4.60; %S 12.20.

Ir Spectrum (potassium bromide): Bands at 1,740, 1600, 1200, 870, 720 and 700$cm^{-1}$.

U. V. Spectrum (ethanol): Max. at 304 and 268 mμ.

Salification of the said acid with diisopropylamine resulted in the corresponding diisopropylamine salt melting at 104°–106° C.

As far as is known, these compounds are not described in the literature.

EXAMPLE 2

5-(p-chlorobenzoyl)-thiophene-2-α-methyl acetic acid.

Using the procedure of Example 1, 12.49 gm of thiophene-2-α-methyl acetic acid, 16.80 gm of p-chlorobenzoyl chloride and 28.8 gm of aluminum chloride were reacted to obtain after crystallization from benzene a 45% yield of 5-(p-chlorobenzoyl)-thiophene-2-α-methyl acetic acid melting at 149° C. The product occurred in the form of colorless crystals soluble in N sodium hydroxide and ethyl acetate and insoluble in water.

Analysis: $C_{14}H_{11}O_3Cl\,S$; molecular weight = 294.75. Calculated: %C 57.04; %H 3.76; %Cl 12.03; %S 10.88. Found: %C 57.10; %H 3.70; %Cl 11.80; %S 11.00.

IR spectrum (potassium bromide): Bands at 1700, 1620, 1230, 870, 840, and 750$cm^{-1}$.

U.V. Spectrum (ethanol): Max. at 305 mμ.

As far as is known, this compound is not described in the literature.

EXAMPLE 3

5-hexahydrobenzoyl-thiophene-2-α-methyl acetic acid.

Using the procedure of Example 1, 18.72 gm of thiophene-2-α-methylacetic acid, 21 gm of hexahydrobenzoyl chloride and a suspension of 43.2 gm of aluminum chloride in 205 cc of chloroform were reacted to obtain after crystallization form hexane, 12 gm (37% yield) of 5-hexahydrobenzoyl-thiophene-2-α-methylacetic acid melting at 98° C. The product occurred in the form of colorless crystals soluble in dilute aqueous alkalis, acetone and ethyl acetate and insoluble in hexane and water.

Analysis: $C_{14}H_{18}O_3S$; molecular weight =266.34. Calculated: %C 63.13; %H 6.81; %S 12.04. Found: %C 63.20; %H 6.60; %S 12.10.

IR Spectrum (potassium bromide): Bands at 1700, 1640, 1255, 820 and 770$cm^{-1}$.

U.V. Spectrum (ethanol): Max. at 293 and 265 mμ.

As far as is known, this compound is not described in the literature.

EXAMPLE 4

5-(α-thenoyl)-thiophene-2-α-methylacetic acid.

Using the procedure of Example 1, 9.37 gm of thiophene 2-α-methyl-acetic acid, 10.55 gm of α-thenoyl chloride and 21.6 gm of aluminum chloride suspended in chloroform were reacted to obtain, after crystallization from isopropyl ether, a 45% yield of 5-(α-thenoyl)- thiophene-2-α-methylacetic acid melting at 113° C. The product is in the form of colorless crystals soluble in dilute aqueous alkalis and insoluble in water.

Analysis: $C_{12}H_{10}O_3S_2$; molecular weight=266.33. Calculated: %C 54.11; %H 3.78; %S 24.08. Found: %C 54.30; %H 4.0; %S 23.90.

I.R. Spectrum (potassium bromide): Bands at 1680, 1600, 1220, 1055, 860, 790 and 730 $cm^{-1}$.

U.V. Spectrum (ethanol): Max. at 320 and 270 mμ.

As far as is known, this compound is not described in the literature.

EXAMPLE 5

5-benzoyl-thiophene-2-acetic acid.

Using the procedure of Example 1, 8.45 gm of benzoyl chloride, 7.1 gm of thiophene-2-acetic acid [prepared by process of Cagniant, Bull. Soc. Chim., 1949, p.847] and 18 gm aluminum alumina chloride suspended in chloroform were reacted to obtain, after crystallization, a 50% yield of 5-benzoyl-thiophene-2-acetic acid melting at 144° C. The product occurred in the form of colorless crystals insoluble in water.

Analysis: $C_{13}H_{10}O_3S$: molecular weight = 246.28. Calculated: %C 63.39; %H 4.09; %S 13.02. Found: %C 63.1; %H 4.0; %S 12.7.

IR Spectrum (potassium bromide): Bands at 1700, 1610 and 1220 $cm^{-1}$.

U.V. Spectrum (ethanol): Max. at 302 and 260 mμ.

As far as is known, this compound is not described in the literature.

EXAMPLE 6

5-(m-trifluoro methyl benzoyl)-thiophene-2-acetic acid.

Using the procedure of Example 1, 7.1 gm of thiophene-2-acetic acid and 10.40 gm of m-trifluoromethyl-benzoyl chloride were reacted to obtain 5(m-trifluoromethyl-benzoyl)-thiophene-2-acetic acid melting at 120° C.

As far as in knwon, this compound is not described in the literature.

EXAMPLE 7

5-(β-nicotinoyl)-thiophene-2-α-methylacetic acid.

Using the procedure of Example 1. 10.3 gm thiophene-2-α-methylacetic acid and 8.50 gm of nicotinoyl acid chloride were reacted to obtain 5-(β-nicotinoyl)-thiophene-2-α-methylacetic acid.

As far as is known, this compound is not described in the literature.

EXAMPLE 8

Methyl 5-(m-trifluoromethyl benzoyl)-thiophene-2-acetate 1.60 gm of 5-(m-trifluoromethylbenzoyl)-thiophene-2-acetic acid were dissolved in 30 cc of methanol and the solution was saturated with gaseous hydrochloric acid and refluxed for 1 hour. The solvent was then distilled off under reduced pressure and the residue was taken up in a minimum of isopropyl ether. An equal volume of petroleum ether was added to the solution. Crystallization was induced by scratching and the solution was iced for 12 hours. The crystals were separated, washed with petroleum ether and dried to obtain 1.35 gm of methyl 5-(m-trifluoromethyl benzoyl)-thiophene-2-acetate.

As far as is known, this compound is not described in the literature.

EXAMPLE 9

2,3-dihydroxypropyl 5-(m-trifluoromethyl benzoyl)-thiophene-2-acetate.

STEP A: 0.65 gm of methyl 5-(m-trifluoromethyl benzoyl)-thiophene-2-acetate were dissolved with agitation in 5 cc of pyridine and then 0.60 gm of 2,2-dimethyl-4-hydroxymethyl-1,3-dioxolane were added thereto followed by addition of 2 cc of a molar solution of sodium methanolate in methanol. The mixture was refluxed for 1½ hour and was then cooled. Excess sodium methanolate was decomposed by the addition of 10cc of 50% acetic acid and the reaction mixture was diluted with 100 cc of ice water. The precipitate formed was recovered by filtration and was washed with water and then with 5% acetic acid and finally with water until the wash waters were neutral and dried. The raw product was purified by crystallization from ethanol to obtain the 2,2-dimethyl-1,3-dioxalane-4-methyl 5-(m-trifluoromethylbenzoyl)-thiophene-2-acetate.

As far as is known, this compound is not described in the literature.

STEP B: The said ester of STEP A was suspended in 20 cc of water and 20 cc of 10% hydrochloric acid were added thereto. The mixture was heated at 90° C. for 15 minutes and after cooling the reaction mixture to room temperature, the precipitate formed was recovered by vacuum filtration. The precipitate was washed with water, dried and crystallized from methylene chloride to obtain 2,3-dihydroxypropyl 5-(m-trifluoromethyl benzoyl)-thiophene-2-acetate.

As far as is known, this compound is not described in the literature.

EXAMPLE 10

Diethylaminoethyl 5-(p-chlorobenzoyl)-thiophene-2-α-methylacetate.

3.2 cc of thionyl chloride were added slowly with stirring to a solution of 0.60 gm of 5-(p-chlorobenzoyl)-thiophene-2-α-methylacetic acid in 20 cc of chloroform and the mixture was refluxed for 3 hours. The chloroform and excess thionyl chloride were distilled off under a nitrogen atmosphere with stirring. The residue was added to 25 cc of ether which was then stirred for 1 hour. The mixture was added to a solution of 2 gm of diethylaminoethanol in 20 cc of ether and agitation was continued for 2 hours. The solid hydrochloride of diethylaminoethanol was removed by filtration and the filtrate was evaporated to dryness under reduced pressure. The residue was dissolved in 20 cc of hot isopropyl ether and the volume was reduced in half and crystallization was effected by cooling to obtain diethylamino ethyl 5-(p-chlorobenzoyl)-thiophene-2-α-methylacetate melting at 112° C.

As far as is known, this compound is not described in the literature.

EXAMPLE 11

5-(α-furoyl)- thiophene-2-α-methylacetic acid.

Using the procedure of Example 1, 12.5 gm of thiophene-2-α-methylacetic acid and 12.5 gm of α-furoyl chloride were reacted to obtain, after crystallization from isopropylether, a 45% yield of 5-(α-furoyl)-thiophene-2-α-methylacetic acid melting at 86° C.

As far as is known, this compound is not described in the literature.

EXAMPLE 12

Methyl 5-benzoyl-thiophene-2-α-methyl acetate.

Using the process of Example 8, 15 g, of 5-benzoyl-thiophene-2-α-methylacetic acid and 200 cc of methanol were reacted to obtain an 81% yield of methyl 5-benzoyl-thiophene-2-α-methylacetate boiling at 173°–174° C. at 0.3 mm Hg.

As far as is known, this compound is not described in the literature.

EXAMPLE 13

2,3-dihydroxypropyl 5-benzoyl thiophene-2-α-methyl acetete.

STEP A: Using the process of Example 9, 12.7 gm of methyl 5-benzoyl-thiophene-2-α-methylacetate and 60.8 gm of 2,2-dimethyl-4-hydroxymethyl-1,3-dioxolane were reacted to obtain a 25% yield of the (2,2-dimethyl-1,3-dioxolane-4-methyl) 5-benzoyl-thiophene-2-α-methylacetate melting at 83° C. after recrystallization from isopropanol.

As far as is known, this compound is not described in the literature.

STEP B: The ester in step A was reacted as in Step B of Example 9 to obtain an 84% yield of 2,3-dihydroxypropyl 5-benzoyl-thiophene-2-α-methylacetate melting at 60° C.

As far as is known, this compound is not described in the literature.

EXAMPLE 14

5-(2',4'-dichlorobenzoyl)-thiophene-2-α-methylacetic acid.

Using the procedure of Example 1, 4.7 gm of thiophene-2-α-methyl acetic acid, 6.3 gm of 2,4-dichlorobenzoyl chloride and 10.9 gm of aluminum chloride were reacted to obtain, after crystallization from ethyl acetate, a 33% yield of 5-(2',4'-dichlorobenzoyl)-thiophene-2-α-methylacetic acid melting at 140° C.

As far as is known, this compound is not described in the literature.

EXAMPLE 15

3-methyl-5-benzoyl-thiophene-2-α-methylacetic acid.

STEP A: A mixture of 115 cc of a solution of 0.72 M of methyl magnesium iodide in ether and a solution of 5.87 gm of 3-methyl-thiophene-2-glyoxylic acid [obtained by process of Beil, Vol. 18, p. 409] in 145 cc of ether was agitated for 1 hour and they was allowed to stand overnight. The reaction mixture was added to a mixture of 200 gm of ice and 48 cc of concentrated hydrochloric acid and the mixture was extracted with ether. The ether extracts were washed with water, dried over magnesium sulfate, treated with carbon, filtered and evaporated to dryness under reduced pressure. The residue was dissolved in 35 cc of an aqueous 10% potassium carbonate solution which was then extracted with ether. The aqueous phase was treated with carbon, traces of ether were removed under reduced pressure and the mixture was filtered. The pH of the filtrate was adjusted to 1 by addition of ½ hydrochloric acid and the filtrate was extracted with ether. The ether phase was washed with water, dried over magnesium sulfate, treated with carbon, filtered and evaporated to dryness under reduced pressure to obtain 5.91 gm of 3-methyl-thiophene-2-α-methyl-α-hydroxy acetic acid melting at 86°–87° C. The product occurred as a solid having a light ochae color which was soluble in water, ether and benzene.

Analysis: $C_8H_{10}O_3S$: molecular weight = 186.23. The sulfur content was 99.9–99.85% of theory.

IR Spectrum: Bands at 3400, 3000, 1730, 1460, 1260, 1140 and 720 $cm^{-1}$.

As far as is known, this compound is not described in the literature.

STEP B: A suspension of 28.2 gm of stannous chloride and a solution of 11.2 gm of 3-methyl-thiophene-2-α-methyl-α-hydroxy acetic acid in 300 cc of acetic acid was stirred and then cooled. A current of gaseous hydrochloric acid was passed therethrough for 2 hours and the mixture was then evaporated to dryness. 300 cc of ether were added and then evaporated and the residue was taken up in 60 cc of water with stirring. After cooling, the mixture was vacuum filtered and the precipitate was washed with water and dissolved in 300 cc of ether. The ether phase was washed with water, dried over magnesium sulfate, treated with carbon, filtered and evaporated to dryness under reduced pressure. The residue was dissolved in 50 cc of an aqueous 10% potassium carbonate solution which was then treated with carbon and filtered. The pH of the solution was adjusted to 1 with ½ hydrochloric acid and the solution was extracted with ether. The ether phase was washed with water, dried over magnesium sulfate, filtered and evaporated to dryness under reduced pressure. The residue was triturated in 25 cc of hexane and the mixture was vacuum filtered. The solids were washed with hexane and dried to obtain 6.46 gm of 3-methyl-thiophene-2-α-methylacetic acid melting at 80°–81° C. The product occurred as a colorless solid soluble in ether, benzene, ethanol and chloroform, slightly soluble in water and insoluble in hexane.

Analysis: $C_8H_{10}O_2S$; molecular weight = 170.23. Sulfur was present in 97.4–97.35% of theory.

IR Spectrum: Bands at 3100, 2980, 2940, 1700, 1450, 1380, 1240, 1160, 910 and 715 $cm^{-1}$.

As far as is known, this compound is not described in the literature.

STEP C: 12.9 gm of aluminum chloride were added to 60 cc of dichloroethane and 6.1 gm of 3-methyl-thiophene-2-α-methylacetic acid were added with stirring to the solution which was then stirred for 15 minutes and cooled to 15° C. 5.05 gm of benzoyl chloride were added to the reaction mixture which was stirred for 3 hours at room temperature and then added to a mixture of 150 gm of ice and 25 cc of hydrochloric acid. 150 cc of dichloroethane were added to the mixture and the organic phase was decanted off. The aqueous phase was extracted with dichloroethane and the organic phase was washed with water, dried over magnesium sulfate, treated with carbon, filtered and evaporated to dryness. The residue was taken up in 75 cc of an aqueous 10% potassium carbonate solution and the solution was extracted with ether. The aqueous phase was treated with carbon and traces of ether were removed under vacuum. The mixture was vacuum filtered and the pH of the filtrate was adjusted to 1 by the addition of 1N hydrochloric acid. The solution was extracted with ether and the ether extracts were washed with water until the wash waters were neutral, dried over magnesium sulfate, treated with carbon, filtered and evaporated to dryness under reduced pressure to obtain 7.78 gm of 3-methyl-5-benzoyl-thiophene-2-α-methylacetic acid melting at 100°–101° C. The product occurred in the form of colorless crystals soluble in ether, ethanol and benzene and insoluble in water.

IR Spectrum: Bands at 3160, 3070, 2940, 1720, 1610, 1450, 1300, 855 and 720 $cm^{-1}$.

As far as is known, this compound is not described in the literature.

EXAMPLE 16

4-methyl-5-benzoyl-thiophene-2-acetic acid.

STEP A: 220 cc of thionyl chloride were progressively added to 50 gm of 4-methyl-thiophene-2-carboxylic acid [prepared by process in Beil, Vol. 18, p. 294] and the mixture was heated to reflux for 1 hour. Excess thionyl chloride was evaporated off under reduced pressure and the residue was distilled under reduced pressure to obtain 51 gm of 4-methyl-thiophene-2-carboxylic acid chloride boiling at 112°–114° C. at 18 mm Hg. which was used as is for the next step. The light yellow liquid was soluble in ether.

Analysis: $C_6H_5OSCl$; molecular weight = 160.50. Calculated: %Cl 22.1; %S 20. Found: %Cl 22.05/22.07; %S 19.71/19.80.

STEP B: A solution of 27.2 gm of 4-methyl-thiophene-2-carboxylic acid chloride in 230 cc of methylene chloride was added to a methylene chloride solution of 0.427 mole of diazo-methane cooled to −5° C. and after stirring for 30 minutes, the reaction mixture was allowed to stand overnight at room temperature. Excess diazomethane was destroyed by addition of an aqueous 50% acetic acid solution and the mixture was evaporated to dryness under reduced pressure to obtain 32.5 gm of α-diazo-4-methyl-aceto-thienone which was used as is for the next step. The product occurred as yellow crystals melting at 123°–125° C. and soluble in methylene chloride and ethanol and insoluble in ether.

As far as is known, this compond is not described in the literature.

STEP C: A solution of 18.32 gm of silver benzoate in 230 cc of triethyl amine was added to the solution of 32.5 cc of α-diazo-4-acetothiophene and was then stirred for 1 hour. The solution was treated with carbon, heated to its boiling point for a few minutes and then filtered. The solution was evaporated to dryness under reduced pressure and the residue was taken up in 1200 cc of ether and the solution was filtered. The ether phase was washed with water, then with an aqueous 10% sodium bicarbonate solution and finally with water to obtain a solution with a pH of 5. The solution was dried over magnesium sulfate, treated with carbon, filtered and evaporated to dryness under reduced pressure. The oily residue was distilled to obtain a 44% yield of ethyl 4-methyl-thiophene-2-acetate which was used as is for the next step. The product was in the form of a yellow liquid boiling from 74° to 102° C. at 0.4 mm Hg and soluble in ether and ethanol and insoluble in water.

Analysis: $C_9H_{12}O_2S$; molecular weight = 184.26. Sulfur: 97–97.6% of theory.

IR Spectrum: Bands at 3100, 2980, 1720, 1650, 1420, 1200, 1030, 850, 735, and 595 $cm^{-1}$.

As far as is known, this compound is not described in the literature.

STEP D: A mixture of a solution of 16.25 gm of ethyl 4-methyl-thiophene-acetate in 35 cc of ethanol and 132 cc of an ethanolic solution of 1N potassium hydroxide was allowed to stand for 1 hour and was then vacuum filtered. The precipitate was washed with alcohol and then with ether to obtain 8.3 gm of raw product. The filtrate was added to 300cc of ether to obtain a 2nd crop of 3.2 gm of product. The entire 11.5 gm of raw product were dissolved in 55 cc of water and the solution was treated with carbon and filtered. The pH of the filtrate was adjusted to 1 by the addition of 1N hydrochloric acid and after cooling, the solution was extracted with ether. The ether phase was washed with water, dried over magnesium sulfate, treated with carbon, filtered and evaporated to dryness under reduced pressure. The residue was recrystallized from petroleum ether to obtain 6.78 gm of 4-methyl-thiophene-2-acetic acid melting at 49° C. The product occurred in the form of an ochre solid soluble in water, benzene, ethanol and chloroform.

Analysis: $C_7H_8O_2S$; molecular weight = 156.20. Calculated: %C 53.82; %H 5.16; %S 20.53. Found: %C 54.0; %H 5.2; %S 20.2.

U.V. Spectrum: Max. at 236 mμ.

IR Spectrum: Bands at 3100, 2900, 2650, 1700, 1230, 920, 730 and 585 $cm^{-1}$.

As far as is known, this compound is not described in the literature.

STEP E: Using the procedure of Example 15, 6.65 gm of 4-methyl-thiophene-2-acetic acid and 5.96 gm of benzoyl chloride were reacted to obtain 4.87 gm of 4-methyl-5-benzoyl-thiophene-2-acetic acid melting at 86° C. The product occurred as a colorless solid soluble in benzene, ether, ethanol, chloroform and acetone and insoluble in water.

Analysis: $C_{14}H_{12}O_3S$; molecular weight = 260.31. Found: %S 98.65–98.85% of theory Cl — <0.3 gm per 100 gm.

U.V. Spectrum: Max. at 300 and 252 mμ.

IR Spectrum: Bands at 3080, 2920, 2600, 2700, 1700, 1620, 1420, 1380, 1260, 1220, 895, 716 and 688 $cm^{-1}$.

As far as is known, this compound is not described in the literature.

EXAMPLE 17

5-(m-trifluoromethyl-benzoyl)-thiophene-2-α-methylacetic acid

Using the procedure of Example 1, thiophene-2-α-methylacetic acid and m-trifluoromethyl-benzoyl chloride were reacted to obtain 5-(m-trifluoromethylbenzoyl)-thiophene-2-α-methylacetic acid melting at 76° C.

As far as is known, this compound is not described in the literature.

EXAMPLE 18

5-(3′,4′,5′-trimethoxy-benzoyl)-thiophene-2-acetic acid

Using the procedure of Example 1, thiophene-2-acetic acid and 3,4,5-trimethoxybenzoyl-chloride were reacted to obtain 5-(3′,4′,5′-trimethoxybenzoyl)-thiophene-2-acetic acid melting at 124° C.

As far as is known, this compound is not described in the literature.

EXAMPLE 19

5-(p-chlorobenzoyl)-thiophene-2-acetic acid

Using the procedure of Example 1, thiophene-2-acetic acid and p-chlorobenzoyl chloride were reacted to obtain 5-(p-chlorobenzoyl)-thiophene-2-acetic acid melting at 165° C.

As far as is known, this compound is not described in the literature.

EXAMPLE 20

5-(p-methoxybenzoyl)-thiophene-2-α-methylacetic acid

Using the procedure of Example 1, thiophene-2-α-methylacetic acid and p-methoxybenzoyl chloride were reacted to obtain 5-(p-methoxybenzoyl)-thiophene-2-α-methylacetic acid melting at 117° C.

As far as is known, this compound is not described in the literature.

EXAMPLE 21

2-benzoyl-thiophene-3-acetic acid (Formula II, $R_1$=H, $R_2$=H and Ar=phenyl)

28.26 gm of aluminum chloride were mixed with 80 cc of chloroform. A solution of 11.2 gm of thiophene-3-acetic acid (obtained according to the process described by Campaigne et al. J. Am. Chem. Soc. 1948, 70, 1556) in 55 cc of chloroform was added thereto over a period of 10 minutes, then 13.27 gm of benzoyl chloride was added. The reaction mixture was allowed to stand for two hours at room temperature, then it was poured into a mixture of ice and hydrochloric acid. The aqueous mixture was extracted with chloroform. The chloroform phase was washed with water and extracted with an aqueous 10% potassium carbonate solution. This extract was brought to a pH of 1 by the addition of N hydrochloric acid and extracted with ether. The ethereal phase was dried over magnesium sulfate, tested with carbon black, filtered and the ether was evaporated.

17.5 gm of a residue was recovered which was taken up by 30 cc of isopropylether. The 2-benzoyl-thiophene-3-acetic acid crystallized therefrom. 6.5 gm of raw product was obtained. A new crystallization supplied 3.1 gm of 2-benzoyl-thiophene-3-acetic acid in the form of yellow crystals, soluble in ethanol, chloroform and ether, and insoluble in water and isopropylether, melting at 132° C. (Yield 16%).

Analysis: $C_{13}H_{10}O_3S$; molecular weight = 246.27. Calculated: %C 63.39; %H 4.09; %S 13.02. Found: %C 63.4; %H 4.3; %S 12.7.

As far as is known, this compound is not described in the literature.

EXAMPLE 22

5-benzoyl-thiophene-3-acetic acid (Formula II, $R_1$=H, $R_2$=H and Ar=phenyl)

Step A: Raw 5-benzoyl-thiophene-3-acetic acid.

28.26 gm of aluminum chloride were mixed with 80 cc of chloroform. A solution of 11.2 gm of thiophene-3-acetic acid (obtained according to the process described by Campaigne et al. J. Am. Chem. Soc. 1948, 70, 1556) in 55 cc of chloroform was added thereto over a period of 10 minutes, then 13.27 gm of benzoyl chloride was added. The reaction mixture was allowed to stand for two hours at room temperature, then it was poured into a mixture of ice and hydrochloric acid. The aqueous mixture was extracted with chloroform. The chloroform phase was washed with water and extracted with an aqueous 10% potassium carbonate solution. This extract was brought to a pH of 1 by the addition of N hydrochloric acid and extracted with ether. The ethereal phase was dried over magnesium sulfate, treated with carbon black, filtered and the ether was evaporated.

The residue was dissolved in hot isopropylether and the isopropylether was evaporated. 8.8 gm of raw 5-benzoyl-thiophene-3-acetic acid was recovered.

Step B: Methyl 5-benzoyl-thiophene-3-acetate.

9.8 gm of raw 5-benzoyl-thiophene-3-acetic acid were dissolved in 150 cc of methanol. A stream of gaseous hydrochloric acid was bubbled through this solution until the same was saturated. The methanol was evaporated and the residue was taken up in ether. The ethereal phase was washed with an aqueous 10% potassium carbonate solution, then with water until the wash waters were neutral. Thereafter, the ethereal phase was dried over magnesium sulfate, treated with carbon black, filtered and the ether was evaporated. After distillation, 5.45 gm of methyl 5-benzoyl-thiophene-3-acetate were obtained in the form of a colorless liquid, soluble in ether and insoluble in water, boiling at 170°–172° C. under 0.2 mm of Hg.

As far as is known, this compound is not described in the literature.

Step C: 5-benzoyl-thiophene-3-acetic acid.

3.1 gm of methyl 5-benzoyl-thiophene-3-acetate were dissolved in 10 cc of ethanol. 13.4 cc of an N ethanol solution of potassium hydroxide were added thereto and the reaction solution was maintained in the cold for a period of 3 hours. Thereafter, the solution was brought to a pH of 7 by the addition of N hydrochloric acid and the ethanol was evaporated. The residue was taken up in 100 cc of water and acidified to a pH of 1 by the addition of N hydrochloric acid. This aqueous acidic mixture was extracted with ether. The ethereal phases were washed with water until the wash waters were neutral, dried over magnesium sulfate, treated with carbon black, filtered and the ether was evaporated.

The residue was taken up in 5 cc of isopropylether, cooled and filtered. After recrystallization of the precipitate in isopropyl ether, 0.85 gm of 5-benzoyl-thiophene-3-acetic acid were obtained in the form of colorless crystals, soluble in ethanol, chloroform and ether and insoluble in water, melting at 106° C.

Analysis: $C_{13}H_{10}O_3S$; molecular weight = 246.27. Calculated: %C 63.39; %H 4.09; %S 13.02. Found: %C 63.6; %H 4.3; %S 12.8.

As far as is known, this compound is not described in the literature.

PHARMACOLOGICAL STUDY

1. Acute Toxicity

The acute toxicity test was carried out on lots of 10 male mice weighing about 20 gm. The test products suspended in aqueous 5% gum were administered intraperitoneally and/or orally in increasing doses. The average lethal dose ($LD_{50}$) was determined graphically by the method of Dragstedt and Lang after 8 days observation. The results are shown in Table I.

TABLE I

| PRODUCTS | INTRAPERITONEALLY mg/kg | ORALLY |
|---|---|---|
| 5-benzoyl-thiophene-2-α-methylacetic acid | 355 | 732 mg/kg |
| 5-(p-chlorobenzoyl)-thiophene-2-α-methyl-acetic acid | 160 | — |

TABLE I-continued

| PRODUCTS | INTRAPERI-TONEALLY mg/kg | ORALLY |
|---|---|---|
| 5-(hexahydrobenzoyl)-thio-phene-2-α-methyl-acetic acid | 328 | — |
| 5-(α-thenoyl)-thiophene-2-α-methyl acetic acid | 700 | between 1 and 2 gm/kg |
| 5-benzoyl-thiophene-2-acetic acid | 545 | 1 gm/kg |
| 2-benzoyl-thiophene-3-acetic acid | 775 | |
| 5-benzoyl-thiophene-3-acetic acid | 500 | |

2. Anti-inflammatory Activity

The anti-inflammatory activity was determined by the test of arthritis provoked by carraghenin in rats. 0.05 cc of a 1% sterile suspension of carraghenin was administered into the tibio-tarsalis joint of a hind paw of male rats weighing 130 to 150 gm. At the same time, the test product in a 5% gm suspension in gummy water was injected intraperitoneally or given orally to 5 rats for each amount tested. The volume of the paw was measured before the injection and then 2, 4, 6, 8 and 24 hours afterwards. The intensity of the inflammation was at a maximum 4 to 6 hours after the injection of carraghenin. The difference between the volumes of the paws of the treated animals and of the controls proved the anti-inflammatory action of the drug. The products were administered in increasing doses and the following tables summarize the results as the function of the administered dose.

TABLE II a. Intraperitoneally

| PRODUCTS | Doses in mg/kg | % Protection |
|---|---|---|
| 5-benzoyl-thiophene-2-α-methyl acetic acid | 5 | 35 |
| | 20 | 50 |
| 5-(α-thenoyl)-thiophene-2-α-methyl acetic acid | 14 | 40 |
| | 28 | 30 |
| | 140 | 45 |
| 5-benzoyl-thiophene-2-acetic acid | 22 | 32 |
| | 109 | 40 |

TABLE III b. Orally

| PRODUCTS | Doses in mg/kg | % Protection |
|---|---|---|
| 5-benzoyl-thiophene-2-α methyl acetic acid | 2 | 28 |
| | 5 | 50 |
| | 10 | 47 |
| | 25 | 50 |
| 5-(p-chlorobenzoyl)-thio-phene-2-α-methyl acetic acid | 5 | 15 |
| | 10 | 40 |
| 5-benzoyl-thiophene-2- | 5 | 30 |

TABLE III-continued b. Orally

| PRODUCTS | Doses in mg/kg | % Protection |
|---|---|---|
| acetic acid | 25 | 50 |

The same test was repeated with oral ingestion on several lots of 10 animals for each dose and the 50% protective dose ($DA_{50}$) was defined in a high precision. The $DA_{50}$ dose for 5-benzoyl-thiophene-2-α-methyl acetic acid was 10 mg/kg whereas that for 5-benzoyl-thiophene-2-acetic acid was 15 mg/kg.

The same test with intraperitoneal injection on 5 test animals per lot was repeated utilizing 5-benzoyl-thiophene-3-acetic acid and 2-benzoyl-thiophene-3-acetic acid. However, the volume of the paw was measured before the injection, then 3 hours, 4 hours and 5 hours afterwards.

The intensity of the inflammation is maximal 3 to 5 hours after the injection of carraghenin. The difference between the volumes of the paws of the treated animals and the controls proved the anti-inflammatory action of the drug. The products were administered at increasing dosages and the following Table IV summarizes the results.

TABLE IV

| | | Volume of the paw in cc | | | |
|---|---|---|---|---|---|
| Product | Doses | Before the injection of carraghenin | 3 h | 4 h | 5 h |
| | | | After the injection of carraghenin | | |
| Controls | 0 | 1.00 | 1.67 | 1.71 | 1.63 |
| 5-benzoyl-thiophene-3-acetic acid | 20 mg/kg interperitoneally | 1.00 | 1.39 (−42%) | 1.44 (−38%) | 1.46 (−27%) |
| Controls | 0 | 1.03 | 1.67 | 1.66 | 1.64 |
| 5-benzoyl-thiophene-3-acetic acid | 50 mg/kg interperitoneally | 0.95 | 1.30 (−45%) | 1.34 (−38%) | 1.37 (−31%) |

The product studied, as can be noted, possessed an important anti-inflammatory activity at a dose of 20 mg/kg. Under the same conditions, 2-benzoyl-thiophene-3-acetic acid at a dose of 50 mg/kg gave a protection of the same order.

These results show that the products have a considerable anti-inflammatory activity both orally and intraperitoneally. Under the same conditions, aspirin at a dose of 100 mgm/kg administered intraperitoneally caused a 39% decrease of the edema.

3. Analgesic Effect

The test used was based on the fact noted by R. Koster et al (Fed. Proc., 1959, Vol. 18, Page 412) wherein the intraperitoneal injection of acetic acid causes in mice characteristic repeated stretching and twisting movements which can persist for more than six hours. Analgesics prevent or supress this syndrome which, therefore, can be considered as externalization of a diffuse abdominal pain.

A solution of 3% acetic acid in water containing 10% arabic gum was used and the dose which released the syndrome under these conditions was 0.01 cc/gm, that is 300 mg/kg of acetic acid. The test compounds were administered subcutaneously one-half hour before the intraperitoneal injection of acetic acid, the mice having fasted since the night before the experiment. For each dose and for each control, which are obligatory for each test, a group of 5 animals was used. For each mouse, the stretchings were observed and counted and then added for the group of 5 during a period of 15 minutes starting immediately after the injection of acetic acid.

Table V summarizes the results.

TABLE V

| Products | Doses in mg/kg | % Protection |
| --- | --- | --- |
| 5-Benzoyl-thiophene-2-α-methyl acetic acid | 25 | 51 |
| | 125 | 67 |
| 5-(p-chlorobenzoyl-thiophene-2-α-methyl acetic acid | 15 | 43 |
| | 72 | 62 |
| 5-(hexahydrobenzoyl)-thiophene-2-α-methyl-acetic acid | 20 | 37 |
| | 100 | 58 |
| 5-(α-thenoyl)-thiophene-2-α-methyl acetic acid | 28 | 58 |
| | 140 | 72 |
| 5-benzoyl-thiophene-2-acetic acid | 20 | 58 |
| | 100 | 77 |
| 2-benzoyl-thiophene-3-acetic acid | 40 | 20 |
| | 200 | 66 |

These results show that the test products exert a considerable analgesic activity.

In a comparable test, a solution of 1% acetic acid in water, containing arabic gum was used and the dose which released the syndrom under these conditions was 100 mg/kg of acetic acid. The compounds studied were administered orally one-half hour before the intraperitoneal injection of the acetic acid, the mice having fasted since the night before the test. For each dose and for each control, which are obligatory for each test, several groups of 10 animals were used in order to obtain the 50% protective dose (DA$_{50}$) with a high precision. The amount of stretchings were determined as above. The DA$_{50}$ dose for 5-benzoyl-thiophene-2-α-methyl acetic acid was 2 mg/kg and that for 5-benzoyl-thiophene-2-acetic acid was 25 mg/kg.

Various modifications of the products and process of the invention may be made without departing from the spirit or scope thereof and it is to be understood that the invention is to be limited only as defined in the appended claims.

We claim:

1. A thiophene-acetic acid compound of the formula selected from the group consisting of

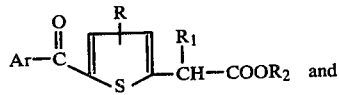

and

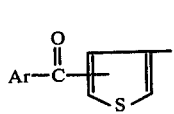

wherein R is selected from the group consisting of hydrogen and methyl, R$_1$ is selected from the group consisting of lower alkyl of 1 to 4 carbon atoms and hydrogen and R$_2$ is selected from the group consisting of hydrogen, lower alkyl of 1 to 7 carbon atoms, 2,3-dihydroxy-propyl, di-lower alkylamino-lower alkyl, alkali metals, alkaline earth metals, aluminum and —H, NH (lower alkyl)$_2$ and Ar is selected from the group consisting of phenyl, phenyl substituted with a member selected from the group consisting of chlorine, methoxy and trifluoromethyl; wherein the second formula

is attached to one of the positions α to the sulfur atom.

2. A compound of claim 1 which has at least one asymmetrical carbon and is in racemic form or an optically active isomer.

3. A compound of claim 1 wherein R is hydrogen.

4. A compound of claim 1 which is 5-benzoyl-thiophene-2-α-methyl acetic acid.

5. A compound of claim 1 which is 5-(p-chlorobenzoyl)-thio-phene-2-α-methyl acetic acid.

6. A compound of claim 1 which is 5-benzoyl-thiophene-2-acetic acid.

7. A compound of claim 1 which is 5-m-trifluoromethylbenzoyl-thiophene-2-acetic acid.

8. A compound of claim 1 which is methyl 5-(m-trifluoromethylbenzoyl)-thiophene-2-acetate.

9. A compound of claim 1 which is 2,3-dihydroxypropyl 5-(m-trifluoromethylbenzoyl)-thiophene-2-acetate.

10. A compound of claim 1 which is diethylamino-ethyl 5-(p-chlorobenzoyl)-thiophene-2-α-methyl acetate.

11. A compound of claim 1 which is diisopropylamine salt of 5-benzoyl-thiophene-2-α-methyl acetic acid.

12. A compound of claim 1 which is methyl 5-benzoyl-thiophene-2-α-methyl acetate.

13. A compound of claim 1 which is 2, 3-dihydroxypropyl 5-benzoyl-thiophene-2-α-methyl acetate.

14. A compound of claim 1 which is 5-(2'4'-dichlorobenzoyl)-thiophene-2-α-methyl acetic acid.

15. A compound of claim 1 which is 3-methyl-5-benzoyl-thiophene-2-α-methyl acetic acid.

16. A compound of claim 1 which is 4-methyl-5-benzoyl-thiophene-2-acetic acid.

17. A compound of claim 1 which is 5-benzoyl-thiophene-3-acetic acid.

18. A compound of claim 1 which is 2-benzoyl-thiophene-3-acetic acid.

19. A compound of claim 1 which is methyl 5-benzoyl-thiophene-3-acetate.

* * * * *